United States Patent
Toyoda et al.

(10) Patent No.: US 8,299,251 B2
(45) Date of Patent: Oct. 30, 2012

(54) METHOD FOR PRODUCING CAMPTOTHECIN DERIVATIVES

(75) Inventors: Asako Toyoda, Tokyo (JP); Hazuki Nagai, Tokyo (JP); George Ng'ang'a Wanyoike, Tokyo (JP)

(73) Assignees: Sichuan Xieli Pharmaceutical Co., Ltd., Sichuan (CN); MicroBiopharm Japan Co., Ltd., Tokyo (JP)

( * ) Notice: Subject to any disclaimer, the term of this patent is extended or adjusted under 35 U.S.C. 154(b) by 220 days.

(21) Appl. No.: 12/994,950

(22) PCT Filed: May 22, 2009

(86) PCT No.: PCT/JP2009/059825
§ 371 (c)(1),
(2), (4) Date: Nov. 29, 2010

(87) PCT Pub. No.: WO2009/145282
PCT Pub. Date: Dec. 3, 2009

(65) Prior Publication Data
US 2011/0112298 A1    May 12, 2011

(30) Foreign Application Priority Data
May 29, 2008    (JP) ................. 2008-140942

(51) Int. Cl.
*C07D 491/22* (2006.01)

(52) U.S. Cl. .................................................... 546/48
(58) Field of Classification Search ............. 546/48
See application file for complete search history.

(56) References Cited

U.S. PATENT DOCUMENTS
2007/0149783 A1    6/2007 Palle et al.

FOREIGN PATENT DOCUMENTS
| JP | 59-005188 | 1/1984 |
| JP | 2848958 | 11/1998 |
| JP | 2007-501275 | 1/2007 |
| WO | 92/05785 | 4/1992 |
| WO | 2004/100897 | 11/2004 |

OTHER PUBLICATIONS

International Search Report issued Aug. 11, 2009 in corresponding International (PCT) Application No. PCT/JP2009/059825, of record.
International Preliminary Report on Patentability and English translation of the Written Opinion issued Jan. 11, 2011 in corresponding International (PCT) Application No. PCT/JP2009/059825.
Sugasawa, T. et al., "Experiments on the Synthesis of *dl*-Camptothecin. III. Total Synthesis of *dl*-Camptothecin", Chem. Pharm. Bull., 1974, vol. 22, No. 4, pp. 771-781.
Wood, J. L. et al., "An Efficient Conversion of Camptothecin to 10-Hydroxycamptothecin", J. Org. Chem., 1995, vol. 60, No. 17, pp. 5739-5740.
Sawada, S. et al., "Synthesis and Antitumor Activity of 20(S)-Camptothecin Derivatives: A-Ring Modified and 7,10-Disubstituted Camptothecins", Chem. Pharm. Bull., 1991, vol. 39, No. 12, pp. 3183-3188.
Shaw, J. E. et al., "Regiospecific Hydrogenation of Quinolines and Indoles in the Heterocyclic Ring", J. Heterocyclic Chem., 1987, vol. 24, pp. 1477-1483.

*Primary Examiner* — Charanjit Aulakh
(74) *Attorney, Agent, or Firm* — Wenderoth, Lind & Ponack, L.L.P.

(57) ABSTRACT

The invention offers a method of hydrogenating camptothecin in inert solvent in the presence of nickel catalyst, whereby selective hydrogenation of camptothecin can be very efficiently accomplished using the low-cost catalyst.

8 Claims, No Drawings

METHOD FOR PRODUCING CAMPTOTHECIN DERIVATIVES

TECHNICAL FIELD

This invention relates to a method for selectively hydrogenating camptothecin or camptothecin derivatives to produce corresponding 1,2,6,7-tetrahydro compounds. The 1,2,6,7-tetrahydro compounds can be utilized as, for example, precursors for synthesizing 10-hydroxy-20-(S)-camptothecin.

BACKGROUND ART

10-Hydroxy-20-(S)-camptothecin is known to have a pharmacological activity itself (cf., for example, Non-patent Document 1) and also is serviceable as a starting material for synthesizing 7-ethyl-10-hydroxy-20-(S)-camptothecin which is an important intermediate in the synthesis of irinotecan. In the Non-patent Document 1, 10-hydroxy-20-(S)-camptothecin is prepared by a two-step procedure via photo-reaction of camptothecin-1-oxide. The previously proposed process for preparation of 10-hydroxy-20-(S)-camptothecin involved oxidizing 1,2,6,7-tetrahydro-20-(S)-camptothecin, using an oxidizing agent selected from the group consisting of lead tetraacetate, CAN (cerium ammonium nitrate), Fremy's salt (potassium nitroso disulfonate $(KSO_3)_2NO$), chromic acid or anhydride, dichromate salts, potassium permanganate, ferric chloride and iodosobenzene diacetate (Patent Documents 1 and 2). Patent Document 1 discloses that 1,2,6,7-tetrahydro-20-(S)-camptothecin which is the starting material can be obtained by hydrogenation of 20-(S)-camptothecin in acetic acid or dioxane-acetic acid in the presence of a platinum catalyst at ambient pressure and temperature.

On the other hand, Patent Document 2 refers to the process of said Patent Document 1 and indicates the following: "Such a method is not fully satisfactory, however, due to the fact that the hydrogenated product is reactive. Hydrogenation therefore continues beyond the preparation of the desired tetrahydrocamptothecin product, resulting in the formation of over-reduction products. Additionally, while the use of a supra-atmospheric hydrogen pressure, although not disclosed in the Japanese patent publication, would be desirable from the standpoint of obtaining a more rapid reaction and/or enhanced conversion of the camptothecin starting material, it has been found that such pressures may not effectively be employed in a process such as that of the Japanese patent due to a further increase in the formation of over-reduction products". With the view to improve the defect in the hydrogenation method of the Patent Document 1, Patent Document 2 proposes to use a noble metal catalyst in the presence of a hydrogenation catalyst moderator selected from hydrogenation catalyst poisons such as dimethylsulfoxide, or to use the noble metal catalyst in combination with a special carrier such as 5% platinum-on-sulfided carbon.

It is also known that 7-ethyl-1,2,6,7-tetrahydro-20-(S)-camptothecin can be obtained by contacting 7-ethyl-20-(S)-camptothecin with hydrogen and noble metal catalyst in the presence of a hydrogenation catalyst moderator selected from hydrogenation catalyst poisons such as dimethylsulfoxide (cf. Patent Document 3).

Results of studying the use of a large variety of heterogeneous catalysts in hydrogenation of quinolines, which can be regarded as a model reaction for selective hydrogenation of camptothecins having quinoline skeletal structure, have been reported (Non-patent Document 2). This document suggests necessity of concurrent use of a sulfur compound (e.g., $CS_2$, $H_2S$) or CO with a noble metal catalyst and nickel catalyst for selectively hydrogenating the heterocyclic ring (pyridine ring) only of quinolines, in conformity with the selective hydrogenation of camptothecins as described in Patent Documents 2 and 3.

PRIOR ART

[Patent Document 1] JP 59(1984)-5188A
[Patent Document 2] JP 2,848,958, in particular, col. 23, L. 1-28
[Patent Document 3] JP 2007-501275T
[Non-patent Document 1] Sawada et al., Chem. Pharma Bull. 39(12) 3183-3188 (1991)
[Non-patent Document 2] Shaw et al., J. Heterocyclic Chem., 24, 1477-1483 (1987)

SUMMARY OF THE INVENTION

Problem to be Solved by the Invention

Conventional hydrogenation of camptothecin invariably uses costly noble metal catalyst such as of platinum. Moreover, the method described in, for example, Patent Document 1 discloses the hydrogenation can be performed at ambient pressure and temperature, but it is subject to a problem that the reduction continues even after formation of object tetrahydrocamptothecin to form over-reduction products.

Patent Documents 2 and 3 proposed, as a means to improve the above method, to carry out the hydrogenation reaction in the concurrent presence of a hydrogenation catalyst moderator such as dimethylsulfoxide, for example, to suppress or curtail the formation of over-reduction products. These processes, however, have a problem that they require use of a much larger amount (about 50 wt % to the substrate) than the usual of a noble metal catalyst. Furthermore, our reproduction of these reduction reactions has now confirmed that the reaction control is difficult also in the cases wherein a hydrogenation catalyst moderator is concurrently present, as the over-reaction is still apt to take place depending on agitation efficiency, reaction pressure or reaction temperature.

Hence, a method for synthesis of 1,2,6,7-tetrahydro-20-(S)-camptothecin derivatives, which can be used on commercial scale, at low cost and is easy of controlling the reaction is in demand.

Means for Solving the Problem

With the view to solve the above problem, we have concentratively advanced our studies, to make a surprising discovery that 1,2,6,7-tetrahydrocamptothecin or 1,2,6,7-tetrahydro-camptothecin derivatives can be prepared with high efficiency when camptothecin or camptothecin derivatives are contacted with hydrogen in the presence of a nickel catalyst, without concurrent presence of such a sulfur compound or the like as described in the above.

The invention, therefore, is completed based on the above discovery and provides a method comprising reduction of a compound represented by the following formula (I), more specifically camptothecin or a camptothecin derivative, to produce the corresponding 1,2,6,7-tetrahydro compound represented by the following formula (II), more specifically 1,2,6,7-tetrahydro-camptothecin or a 1,2,6,7-tetrahydrocamptothecin derivative, which method comprising a step of contacting a compound of the formula (I) with hydrogen in an inert solvent, in the presence of a nickel catalyst as a hydrogenation catalyst:

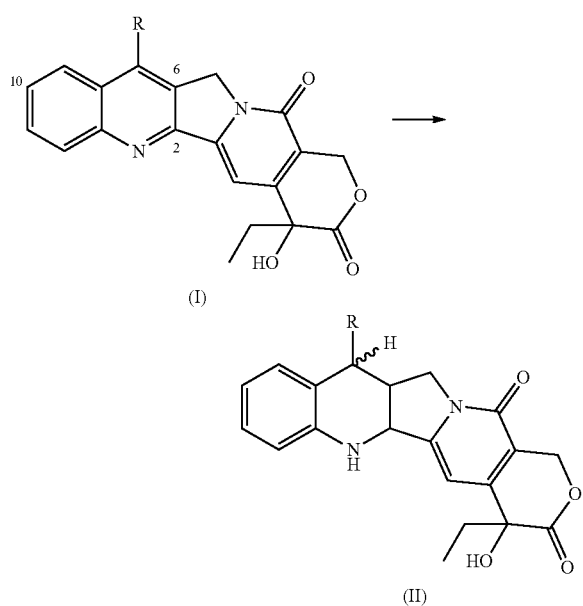

in the formulae, R stands for an atom or an atomic group selected from the group consisting of hydrogen atom and $C_1$-$C_6$ alkyl groups.

Effect of the Invention

According to the invention, the object 1,2,6,7-tetrahydro compounds represented by the above formula (II) can be produced with high efficiency, using a nickel catalyst which is markedly cheaper than noble metal catalyst and in a simple reaction system wherein concurrent use of a hydrogenation catalyst moderator such as a sulfur compound or the like is unnecessary.

EMBODIMENTS FOR WORKING THE INVENTION

The starting camptothecin represented by the formula (I) may be an extract of natural source, semi-synthetic or totally synthetic material. Also its 7-alkyl derivatives can be those prepared from camptothecin by a method known per se. $C_1$-$C_6$ alkyl in the alkyl derivatives may be either of straight chain or branched, and include methyl, ethyl, n-propyl, isopropyl, n-butyl, iso-butyl, t-butyl, n-pentyl, n-hexyl and so on.

Any nickel catalyst such as metallic powder, alloy with other metal(s), oxide, hydroxide, inorganic salt, organic salt or Raney catalyst of nickel metal or those supported on carriers can be used in the present invention, so long as they conform to the purpose of the invention and can efficiently catalyze the hydrogenation reaction. Although not given in limitative sense, as the carriers for the supported type catalyst, diatomaceous earth, silica, alumina ($Al_2O_3$) complex oxide, zeolite and the like can be named. Supported type catalyst is preferred as it enables the use of lesser amount of the metal, and also from the standpoint of activation or stable use.

Examples of such catalyst include nickel catalysts known in the pertinent technical field, such as metal nickel, reduced nickel, stabilized nickel, nickel-diatomaceous earth, Raney nickel, modified Raney nickel, nickel formate, Urushibara nickel, nickel borate, nickel oxide, nickel complex, nickel-copper-diatomaceous earth, nickel-zirconia-diatomaceous earth, nickel-alumina, nickel-silica-alumina, nickel-cobalt, nickel-copper-cobalt, nickel-iron, nickel-iron-cobalt, nickel-iron-phosphorus, nickel oxide-silica, nickel oxide-magnesium oxide-alumina and nickel oxide-molybdenum trioxide-alumina.

Of these, stabilized nickel catalyst on diatomaceous earth as the carrier exhibits adequate catalytic activity in the reaction and therefore is preferred.

Stabilized nickel catalyst refers to the one which is prepared by once completely reducing nickel oxide and thereafter oxidizing the reduced nickel surface, whereby protecting the reduced nickel with the oxidized surface film. Differently from ordinary reduced nickel catalyst, there is little risk of its oxidation or heat generation when it is exposed to air and, furthermore, it is so prepared as to exhibit sufficient hydrogenation activity when it is used in hydrogenation reactions as it is. One in which a minor amount of cocatalyst is concurrently present for enhancing resistance to organosulfur compound which acts as a fatal catalyst poison to nickel catalyst (sulfur-resistant stabilized nickel) is also included in the scope of stabilized nickel catalyst.

Examples of preferred stabilized nickel catalyst include those supported on diatomaceous earth, each one of which contains 5-80 wt % of nickel in terms of nickel or nickel oxide, optionally containing in addition thereto 0.1-10 wt % of one or more substances suitably selected from copper, chromium, manganese, iron, cobalt, zinc, aluminium, molybdenum, tungsten or oxides thereof as the cocatalyst. In particular, such a catalyst which contains 40-60 wt % of nickel in terms of nickel or nickel oxide and optionally further contains 1-5 wt % of one or more substances suitably selected from copper, chromium, manganese, iron, cobalt, zinc, aluminium, molybdenum, tungsten or their oxides as the cocatalyst, is advantageous. Specifically, commercialized stabilized nickel catalysts, N111, N112, N113, N113B, N103, N103B and N103K (NIKKI CHEMICAL CO. LTD.); SN-110, SN-150, SN-250, SN-300 and SN-750 (Sakai Chemical Industry); and Ni-5123P, Ni-5136P, Ni-5256P, Ni-0104T, Ni-3266, Ni-3288E, Ni-3737T and Ni-5256E (N.E. Chemcat) are preferred. Of those, particularly preferred stabilized nickel catalysts are N113 (the catalyst in which a mixture of nickel 18%, nickel (II) oxide 39%, copper (II) oxide 2% and chromium (III) oxide 2% is supported on diatomaceous earth 26%) (NIKKI CHEMICAL CO. LTD.) or N-103 (a mixture of nickel 27% and nickel (II) oxide 33% is supported on diatomaceous earth 30%) (NIKKI CHEMICAL CO. LTD.); and SN-250 (nickel or nickel (II) oxide 55% is supported on diatomaceous earth) (Sakai Chemical Industry).

The use rate of such a nickel catalyst can be selected to catalyze the reaction intended by the present invention. For instance, when the stabilized nickel catalyst N113 is used as the hydrogenation catalyst, the catalytic amount is about 5-100 wt %, in particular, 10-40 wt %, to camptothecin or a camptothecin derivative which is the substrate.

The inert solvent as referred to in the present invention covers any solvents which do not directly react with the reactants and the catalyst and do not adversely affect the hydrogenation reaction of the invention, and which furthermore are capable of dissolving the product. The solvent may be a mixture of two or more of such solvents at a suitable ratio or ratios. Although not given in a limitative sense, $C_1$-$C_3$ organic acids such as formic acid, acetic acid and propionic acid; or $C_1$-$C_2$ alcohols such as methanol, ethanol; or dioxane; or their mixtures are preferred. Acetic acid is particularly preferred because of its high solubility of camptothecin or camptothecin derivatives and no adverse effect on the reaction system.

Suitable amount of such a solvent is a volume capable of favorably dispersing or diffusing therein the camptothecin or camptothecin derivative which is the substrate, and the catalyst. A preferred amount of the solvent is about 10-50 volumes per volume of the substrate. For instance, where acetic acid is used, it is particularly preferred to use about 10-20 times that of the substrate.

The hydrogenation reaction according to the present invention can be carried out under a suitable hydrogen pressure, preferably under about 0.5 MPa at the least, in particular, within the range of 1-3 MPa.

The temperature at which the reaction is performed can be within a suitable range taking into consideration other conditions such as the kind of the catalyst used, pressurizing condition and so on. Generally preferred range is from room temperature to 200° C., in particular, 90-140° C. Heating can accelerate progress of the reaction, rather than carrying it out at room temperature.

The reaction time cannot be limited, as the optimum conditions vary depending on the reaction pressure, temperature and so on. Generally preferred time is 0.5-24 hours, in particular, 1-10 hours.

The order of contacting the reaction solvent, substrate and nickel catalyst can be selected according to the necessity in individual occasion.

When the starting material is hydrogenated and the product is 1,2,6,7-tetrahydrocamptothecin, four kinds of stereoisomers, which differ in respect of the relative positions of the hydrogen atoms bound to the bridgehead carbon atoms shared by the B and C rings, can be formed. Also when $C_1$-$C_6$ alkyl is bound to 7-position of 1,2,6,7-tetrahydrocamptothecin, eight kinds of stereoisomers can be formed. All of these stereoisomers are included in the scope of the compound represented by the formula (II). Any of these stereoisomers can be used as a starting material for synthesis of, for example, corresponding 10-hydroxy-20-(S)-camptothecin.

Isolation of 1,2,6,7-tetrahydro compound represented by the formula (II) from the reaction mixture can be carried out by any conventional methods, for example, following the method as described in Patent Document 1. It is also possible to filter the reaction mixture to remove the nickel catalyst therefrom, and to subject the residue successively to the next reaction step of converting the 1,2,6, 7-tetrahydrocamptothecin to 10-hydroxycamptothecin without the isolation, as described in Patent Document 2.

Hereinafter the present invention is explained referring to Examples, it being understood that the invention is not limited by the following embodiments. In the Examples, detection or quantitation of products were performed under the following HPLC analysis conditions:
    column: CAPCELL PAK C18 MG II (Shiseido) (4.6 mm I.D.×250 mm, 5 μm)
    mobile phase: A/B=1/1 (A: sodium acetate buffer (pH4.04), B: 5 mM methanol solution of sodium heptasulfonate)
    flow rate: 1.0 mL/min.
    column temp.: 40° C.
    detection: UV254 nm

EXAMPLE 1

Preparation of 1,2,6,7-tetrahydrocamptothecin

In a 350 mL high pressure autoclave, 6 g (17.2 mmol) of camptothecin was suspended in 60 mL of acetic acid, and into which 2.4 g of stabilized nickel catalyst (N113) was added. After substituting the atmosphere in the autoclave with hydrogen, the suspension was heated at 110° C. under 2.0 MPa for 3 hours with stirring, whereat the starting material disappeared. The reaction liquid was cooled off to room temperature, filtered on 3 g of Celite and washed with 30 mL of acetic acid. The filtrate was washed with heptane (once with 80 mL and twice with 60 mL each), extracted with 60 mL of chloroform, and the organic layer was washed successively with 30 mL of water and 30 mL of saturated saline. The organic layer was dried over 2 g of magnesium sulfate, filtered and concentrated. To the resulting orange colored oil, 10 mL of chloroform was added and heated at 35° C. to form a homogeneous solution. Upon adding thereto 10 mL of heptane, a precipitate was formed. Distilling the solvent off under reduced pressure and drying the residue, 5.8 g of 1,2,6,7-tetrahydrocamptothecin was obtained as an orange colored powder (yield: 96.8%, in which the diastereoisomeric ratio* was 21:76).

Note)* Diastereoisomeric ratio means the ratio of RRT 0.62 to RRT 0.9, the numerical values following RRT meaning each the relative retention time where the retention time of camptothecin (CPT) is assumed to be 1. The same applies hereafter.

1,2,6,7-tetrahydro-20-(S)-camptothecin (RRT0.62)

$^1$H-NMR(500 MHz,CDCl$_3$)δ(ppm):7.04(1H,t),6.99(1H, d), 6.69(1H,t),6.61(1H,s),6.60(1H,d),5.57(1H,d),5.16(1H, d), 4.89(1H,t),4.31(1H,04.21(1H,dd),4.08(1H,dd),3.63(1H, s), 2.88(1H,dd),2.84(1H,m),2.45(1H,dd),1.79(2H,m),0.98 (3H,t)

1,2,6,7-tetrahydro-20-(S)-camptothecin (RRT0.90)

$^1$H-NMR(500 MHz,CDCl$_3$)δ(ppm):7.07(1H,7.03(1H,d), 6.72(1H,t),6.64(1H,d),6.60(1H,d),5.59(1H,d),5.13(1H,d), 4.89(1H,t),4.36(1H,d),4.19(1H,dd),4.13(1H,dd),3.65(1H,s), 2.88(1H,dd),2.83(1H,m),2.45(1H,dd),1.77(2H,m),0.94(3H, t)

9,10,11,12-tetrahydro-20-(S)-camptothecin (RRT1.24)

$^1$NMR(500 MHz,CDCl$_3$)δ(ppm):7.64(1H,s),7.43(1H,s), 5.72(1H,d),5.27(1H,d),5.05(2H,s),3.64(1H,s),3.05(2H,t), 2.90(2H,t),1.88(6H,m),1.01(3H,t)

EXAMPLE 2

Preparation of 1,2,6,7-tetrahydrocamptothecin

In a 350 mL high pressure autoclave, 6 g (17.2 mmol) of camptothecin was suspended in 60 mL of acetic acid, and into which 1.2 g of stabilized nickel catalyst (N113) was added. After hydrogen substitution of the inside atmosphere, the suspension was heated at 110° C. under 2.0 MPa for 6 hours with stirring, whereat the starting material disappeared. The reaction liquid was cooled off to room temperature, filtered on 0.5 g of Celite and washed with 10 mL of acetic acid. An HPLC analysis of this solution confirmed that this Example could produce 1,2,6,7-tetrahydrocamptothecin at an yield of 97% (The diastereoisomeric ratio was 23:74).

EXAMPLES 3-14 AND COMPARATIVE EXAMPLES 1-12

Preparation of 1,2,6,7-tetrahydrocamptothecin

Operations similar to those in Example 2 were repeated while varying the reaction temperature, amount of the catalyst, reaction pressure and so on. The results as shown in the following Table were obtained.

Comparative Examples 1-8 are reproduction tests of known methods. In the method of Comparative Example 1 wherein $PtO_2$ was used as the hydrogenation catalyst in the concurrent presence of dimethylsulfoxide as a hydrogenation catalyst moderator, over-reduction could be suppressed and the object 1,2,6,7-tetrahydrocamptothecin could be quantitatively obtained. Whereas, by the method of Comparative Example 2 where no hydrogenation catalyst moderator was used, the starting camptothecin disappeared, the yield of the object product was only 1% due to over-reduction.

The reaction was carried out in Comparative Examples 3-8 by similar method using as the hydrogenation catalyst 10% Pt/C, 5% Pt/C or 5% Pd/C, under concurrent presence or absence of a hydrogenation catalyst moderator. Where the hydrogenation catalyst moderator was used concurrently, in certain cases the starting camptothecin remained and the reaction failed to complete as in Comparative Example 3, or the over-reduction progressed although the starting material remained unreacted as in Comparative Example 7. On the other hand, in all of the Comparative Examples 4, 6 and 8 not using a hydrogenation catalyst moderator, the over-reduction progressed and the yield of object 1,2,6,7-tetrahydrocamptothecin was decreased. These results suggest that the reaction control is occasionally difficult in the methods known in the past.

Comparative Examples 9-12 show the results of carrying out the reaction using other catalysts referring to known methods and also using acetic acid as the solvent.

Examples 3-14 show the results of the reduction using nickel catalysts in accordance with the present invention, in which the amount of each nickel catalyst was 20-40% to the substrate, the reaction pressure was 1-2 MPa, the reaction temperature was 100-120° C. and the reaction time was 2-10 hours. The over-reduction was almost completely avoided and 1,2,6,7-tetrahydrocamptothecin was produced at high yields.

TABLE 1

| | Catalyst Species | Amount of Catalyst % Wt/CPT | DMSO V %/CPT | Pressure MPa | Temperature ° C. | Time Hr | Yield % *4H-CPT(A) RRT0.62 | CPT RRT0.9 | *4H-CPT(B) RRT1.0 | RRT1.24 |
|---|---|---|---|---|---|---|---|---|---|---|
| Comparative Example 1 | $PtO_2$ | 20 | 8 | 0.5 | 65 | 18 | 7 | 91 | 0 | 0 |
| Comparative Example 2 | | | | | | | 1 | 0 | 0 | 0 |
| Comparative Example 3 | 10% Pt/C | 40 | 8 | | | | 6 | 67 | 20 | 0 |
| Comparative Example 4 | | | | | | | 11 | 46 | 0 | 0 |
| Comparative Example 5 | 5% Pt/C | 50 | 8 | | | | 7 | 92 | 1 | 0 |
| Comparative Example 6 | | | | | | | 12 | 59 | 0 | 2 |
| Comparative Example 7 | 5% Pd/C | 40 | 8 | | | | 12 | 38 | 9 | 1 |
| Comparative Example 8 | | | | | | | 11 | 0 | 0 | 5 |
| Comparative Example 9 | $IrO_2$ | 30 | | 2.5 | 110 | 16 | 0 | 0 | >99 | 0 |
| Comparative Example 10 | $Cl(Ph_3P)Rh$ | 30 | | 2.5 | 110 | 16 | 0 | 0 | >99 | 0 |
| Comparative Example 11 | Zn | 30 | | 2.5 | 110 | 16 | 0 | 0 | >99 | 0 |
| Comparative Example 12 | $Fe_2O_3$ | 30 | | 2.5 | 110 | 16 | 0 | 0 | >99 | 0 |

*CPT: 20-(S)-camptothecin
4H-CPT(A): Object product 1,2,6,7-tetrahydro-20-(S)-camptothecin
4H-CPT(B): By-product 9,10,11,12-tetrahydro-(20)-(S)-camptothecin

TABLE 2

| | Catalyst Species | Amount of Catalyst % Wt/CPT | DMSO V %/CPT | Pressure MPa | Temperature ° C. | Time hr | Yield % *4H-CPT (A) RRT0.62 | CPT RRT0.9 | *4H-CPT(B) RRT1.0 | RRT1.24 |
|---|---|---|---|---|---|---|---|---|---|---|
| Example 3 | N103 | 40 | | 2 | 120 | 2 | 22 | 78 | 0 | 0 |
| Example 4 | N113 | | | | | | 21 | 76 | 0 | 3 |
| Example 5 | SN250 | | | | | | 22 | 74 | 0 | 4 |
| Example 6 | N113 | | | | 110 | 2 | 20 | 77 | 0 | 3 |
| Example 7 | N113 | | | | 100 | 2 | 20 | 76 | 1 | 3 |
| Example 8 | SN250 | | | | | | 23 | 72 | 0 | 4 |
| Example 9 | N113 | | | | | 10 | 19 | 72 | 0 | 2 |
| Example 10 | SN250 | | | | | | 22 | 72 | 3 | 3 |
| Example 11 | N113 | | | 1 | 100 | 2 | 17 | 70 | 9 | 4 |

TABLE 2-continued

| | Amount of | | | | | Yield % | | | |
|---|---|---|---|---|---|---|---|---|---|
| | Catalyst Species | Catalyst % Wt/CPT | DMSO V %/CPT | Pressure MPa | Temperature °C. | Time hr | *4H-CPT (A) RRT0.62 | CPT RRT0.9 | *4H-CPT(B) RRT1.24 |
| | | | | | | | | RRT1.0 | |
| Example 12 | SN250 | | | | | | 21 | 74 1 | 4 |
| Example 13 | N113 | 20 | | 2 | 120 | 2 | 19 | 76 1 | 4 |
| Example 14 | SN250 | | | | | | 21 | 73 3 | 4 |

*CPT: 20-(S)-camptothecin
4H-CPT(A): Object product 1,2,6,7-tetrahydro-20-(S)-camptothecin
4H-CPT(B): By-product 9,10,11,12-tetrahydro-(20)-(S)-camptothecin N103: a catalyst wherein a mixture of nickel 18%, nickel (II) oxide 39%, copper (II) oxide 2% and chromium (III) oxide 2% is supported on diatomaceous earth 26% (NIKKI CHEMICAL CO. LTD.)

N113: a catalyst wherein a mixture of nickel 27% and nickel (II) oxide 33% is supported on diatomaceous earth 30% (NIKKI CHEMICAL CO. LTD.)

SN250: a catalyst wherein nickel or nickel (II) oxide 55% is supported on diatomaceous earth (Sakai Chemical Industry)

EXAMPLE 15

Preparation of
7-ethyl-1,2,6,7-tetrahydrocamptothecin

In a high pressure autoclave 0.5 g (0.13 mmol) of 7-ethyl-camptothecin was suspended in 0.5 mL of acetic acid, and into which 20 mg of nickel catalyst N113 was added. After hydrogen substitution of the inside atmosphere, the suspension was heated at 110° C. under 2.0 MPa for 6 hours with stirring, whereat the starting material disappeared. The reaction solution was cooled off to room temperature, filtered through a PTFE filter (ADVANTEC MFS, INC. DISMIC 13JP020AN) and washed with 0.5 mL of acetic acid. The HPLC analysis confirmed that 7-ethyl-1,2,6,7-tetrahydro-camptothecin could be obtained from this solution at a yield of 96%.

7-Ethyl-1,2,6,7-tetrahydro-20-(S)-camptothecin $^1$H-NMR(500 MHz,DMSO-d6)δ(ppm):7.0-6.8(2H,m), 6.6-6.5(2H,m),6.30(1H,s),5.21(1H,s),4.91(1H,m),4.06(1H,m), 3.91(1H,m),3.17(1H,m),3.01(1H,m),1.90(3H,m),1.72 (2H,m), 1.02(3H,t),0.78(3H,t)

The invention claimed is:

1. A method comprising reduction of a compound represented by the following formula (I) to produce the corresponding 1,2,6,7-tetrahydro compound represented by the following formula (II), comprising a step of contacting a compound of the formula (I) with hydrogen in an inert solvent, in the presence of a nickel catalyst as a hydrogenation catalyst:

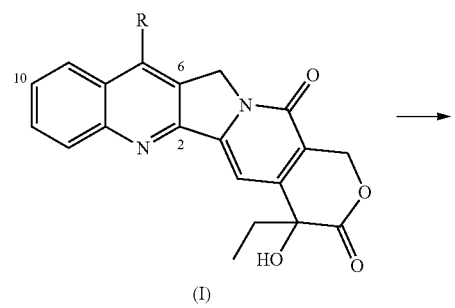

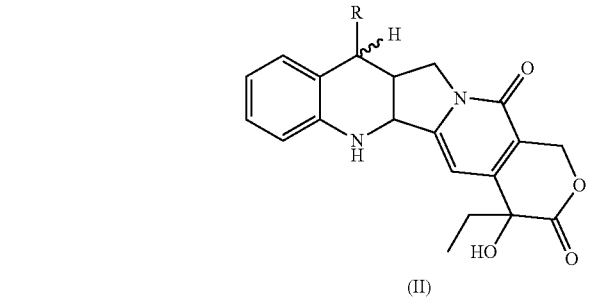

in the formulae, R stands for an atom or an atomic group selected from the group consisting of hydrogen atom and $C_1$-$C_6$ alkyl groups.

2. A production method according to claim 1, in which R is hydrogen atom.

3. A production method according to claim 1, which is characterized in that the nickel catalyst is at least one member selected from the group consisting of metal nickel, reduced nickel, stabilized nickel, nickel-diatomaceous earth, Raney nickel, modified Raney nickel, nickel formate, Urushibara nickel, nickel borate, nickel oxide, nickel complex, nickel-copper-diatomaceous earth, nickel-zirconia-diatomaceous earth, nickel-alumina, nickel-silica-alumina, nickel-cobalt, nickel-copper-cobalt, nickel-iron, nickel-iron-cobalt, nickel-iron-phosphorus, nickel oxide-silica, nickel oxide-magnesium oxide-alumina and nickel oxide-molybdenum trioxide-alumina.

4. A production method according to claim 1, which is characterized in that the nickel catalyst is Raney nickel, modified Raney nickel, or stabilized nickel.

5. A production method according to claim 1, which is characterized in that the nickel catalyst is stabilized nickel.

6. A production method according to claim 2, which is characterized in that the nickel catalyst is at least one member selected from the group consisting of metal nickel, reduced nickel, stabilized nickel, nickel-diatomaceous earth, Raney nickel, modified Raney nickel, nickel formate, Urushibara nickel, nickel borate, nickel oxide, nickel complex, nickel-copper-diatomaceous earth, nickel- zirconia-diatomaceous earth, nickel-alumina, nickel-silica-alumina, nickel-cobalt, nickel-copper-cobalt, nickel-iron, nickel-iron-cobalt, nickel-iron-phosphorus, nickel oxide-silica, nickel oxide-magnesium oxide-alumina and nickel oxide-molybdenum trioxide-alumina.

7. A production method according to claim 2, which is characterized in that the nickel catalyst is Raney nickel, modified Raney nickel, or stabilized nickel.

8. A production method according to claim 2, which is characterized in that the nickel catalyst is stabilized nickel.

* * * * *